(12) United States Patent
Brooks et al.

(10) Patent No.: US 8,764,845 B2
(45) Date of Patent: Jul. 1, 2014

(54) HEAD COMPONENT OF AN ORTHOPAEDIC JOINT PROSTHESIS

(75) Inventors: James Brooks, Leeds (GB); Steven Gowers, Leeds (GB); Jonathan Thompson, Leeds (GB)

(73) Assignee: DePuy International Limited (GB)

( * ) Notice: Subject to any disclaimer, the term of this patent is extended or adjusted under 35 U.S.C. 154(b) by 1311 days.

(21) Appl. No.: 12/593,568

(22) PCT Filed: Mar. 27, 2008

(86) PCT No.: PCT/GB2008/001052
§ 371 (c)(1),
(2), (4) Date: Feb. 23, 2010

(87) PCT Pub. No.: WO2008/117053
PCT Pub. Date: Oct. 2, 2008

(65) Prior Publication Data
US 2013/0184834 A1    Jul. 18, 2013

(30) Foreign Application Priority Data

Mar. 28, 2007  (GB) .................................. 0705911.6

(51) Int. Cl.
*A61F 2/36* (2006.01)
(52) U.S. Cl.
USPC ...................................................... 623/23.11
(58) Field of Classification Search
CPC .................................................... A61F 2/4684
USPC ............ 623/19.11–19.14, 23.11–23.12, 22.4, 623/22.42, 22.11, 22.43–22.46, 23.15
See application file for complete search history.

(56) References Cited

U.S. PATENT DOCUMENTS 2,785,673 A * 3/1957 Anderson .................. 623/23.11
3,053,251 A * 9/1962 Black et al. ................ 623/23.12
(Continued)

FOREIGN PATENT DOCUMENTS

DE    10056698 A1    5/2002
DE    10303660 A1    7/2004
(Continued)

OTHER PUBLICATIONS

PCT International Preliminary Examination Report PCT/GB2008/001052 dated Jul. 14, 2009.
(Continued)

*Primary Examiner* — Alvin Stewart

(57) ABSTRACT

A kit for use in a procedure for implantation of an orthopaedic joint prosthesis includes a head component of an orthopaedic joint prosthesis, which comprises a body part having a convex bearing surface, and a reverse face at which the head component can be connected to a mating component of the joint prosthesis, in which the head component has a chamfer surface extending around at least part of its periphery where the bearing and reverse faces come together, and a plurality of markings on the chamfer surface. The kit includes a trial head component which comprises a body part having a convex trial bearing surface and a reverse face, in which the trial head component has a plurality of markings on the trial bearing surface at or towards the interface between it and the reverse face. The transverse dimensions of the head component are approximately the same as the transverse dimensions of the trial head component, and in which the location of the markings on the chamfer surface around the periphery of the head component corresponds to the location of the markings on the trial bearing surface of the trial head component around its periphery.

16 Claims, 7 Drawing Sheets

(56) References Cited

U.S. PATENT DOCUMENTS

| | | | |
|---|---|---|---|
| 4,911,720 A * | 3/1990 | Collier | 623/23.12 |
| 5,002,581 A | 3/1991 | Paxson | |
| 5,336,268 A * | 8/1994 | Rispeter | 623/22.4 |
| 5,358,526 A * | 10/1994 | Tornier | 623/19.14 |
| 5,405,403 A | 4/1995 | Mikhail | |
| 5,480,451 A | 1/1996 | Grundei | |
| 5,507,824 A * | 4/1996 | Lennox | 623/22.25 |
| 6,197,062 B1 * | 3/2001 | Fenlin | 623/19.12 |
| 6,197,063 B1 * | 3/2001 | Dews | 623/19.14 |
| 6,228,120 B1 * | 5/2001 | Leonard et al. | 623/19.12 |
| 6,283,999 B1 * | 9/2001 | Rockwood, Jr. | 623/19.12 |
| 6,673,114 B2 * | 1/2004 | Hartdegen et al. | 623/19.12 |
| 6,719,799 B1 * | 4/2004 | Kropf | 623/19.14 |
| 6,736,852 B2 * | 5/2004 | Callaway et al. | 623/19.14 |
| 6,749,637 B1 * | 6/2004 | Bahler | 623/19.14 |
| 6,942,699 B2 * | 9/2005 | Stone et al. | 623/19.14 |
| 6,986,790 B2 * | 1/2006 | Ball et al. | 623/19.11 |
| 7,238,207 B2 * | 7/2007 | Blatter et al. | 623/19.14 |
| 7,255,717 B2 * | 8/2007 | Park et al. | 623/23.12 |
| 7,303,585 B2 * | 12/2007 | Horber | 623/19.14 |
| 7,338,528 B2 * | 3/2008 | Stone et al. | 623/19.14 |
| 7,520,902 B2 * | 4/2009 | Deloge et al. | 623/22.15 |
| 7,819,923 B2 * | 10/2010 | Stone et al. | 623/19.14 |
| 7,887,544 B2 * | 2/2011 | Tornier et al. | 606/96 |
| 8,002,838 B2 * | 8/2011 | Klotz | 623/19.14 |
| 8,052,758 B1 * | 11/2011 | Winslow | 623/22.42 |
| 8,062,376 B2 * | 11/2011 | Shultz et al. | 623/19.13 |
| 8,128,705 B2 * | 3/2012 | Birkbeck et al. | 623/23.11 |
| 8,187,282 B2 * | 5/2012 | Tornier et al. | 606/99 |
| 8,231,682 B2 * | 7/2012 | Lafosse et al. | 623/19.11 |
| 8,236,059 B2 * | 8/2012 | Stone et al. | 623/19.14 |
| 8,439,978 B2 * | 5/2013 | Ebbitt | 623/23.12 |
| 2001/0053935 A1 * | 12/2001 | Hartdegen et al. | 623/19.12 |
| 2002/0016634 A1 * | 2/2002 | Maroney et al. | 623/19.14 |
| 2002/0120339 A1 | 8/2002 | Callaway | |
| 2002/0156534 A1 * | 10/2002 | Grusin et al. | 623/19.14 |
| 2003/0028253 A1 * | 2/2003 | Stone et al. | 623/19.14 |
| 2004/0054421 A1 * | 3/2004 | McLean | 623/23.11 |
| 2004/0098134 A1 * | 5/2004 | Meulink | 623/23.52 |
| 2004/0122524 A1 * | 6/2004 | Hunter et al. | 623/22.18 |
| 2004/0143335 A1 * | 7/2004 | Dews et al. | 623/19.14 |
| 2005/0288791 A1 * | 12/2005 | Tornier et al. | 623/19.13 |
| 2006/0259148 A1 * | 11/2006 | Bar-Ziv | 623/19.14 |
| 2007/0250174 A1 * | 10/2007 | Tornier et al. | 623/19.11 |
| 2009/0270993 A1 * | 10/2009 | Maisonneuve et al. | 623/19.14 |
| 2010/0049329 A1 * | 2/2010 | Vio | 623/23.12 |
| 2010/0076561 A1 * | 3/2010 | Emmanuel | 623/19.11 |

FOREIGN PATENT DOCUMENTS

| | | |
|---|---|---|
| EP | 0363019 A2 | 4/1990 |
| FR | 2854320 A1 | 11/2004 |
| WO | WO 9725943 A1 | 7/1997 |
| WO | WO 0040178 A1 | 7/2000 |
| WO | WO 0182843 A2 | 11/2001 |
| WO | WO 03053280 A2 | 7/2003 |
| WO | WO 2005089676 A1 | 9/2005 |
| WO | WO 2006045949 A2 | 5/2006 |

OTHER PUBLICATIONS

PCT Search Report and Written Opinion PCT/GB2008/001052 dated Jul. 15, 2008.

UK Search Report GB0705911.6 dated Jul. 5, 2007.

Anapliotis E; German Patent No. DE 10056698 A1; May 16, 2002; English Abstract; Derwent World Patents Index; Dialog® File No. 351 Accession No. 12450172; © 2009 Derwent Information Ltd.

Anapliotis E., et al.; German Patent No. DE 10303660 A1; Jul. 29, 2004; English Abstract; Derwent World Patents Index; Dialog® File No. 351 Accession No. 14356522; © 2009 Derwent Information Ltd.

Mertl P. et al.; French Patent No. FR 2854320 A1; Nov. 5, 2004; English Abstract; Derwent World Patents Index; Dialog® File No. 351 Accession No. 14617069; © 2009 Derwent Information Ltd.

Metasul® LDH® Large Diameter Head with Durom® Acetabular Component Surgical Technique; Product Brochure; 97-1081-002-00 Rev. 1 © 2007, 2008 Zimmer, Inc.; www.zimmer.com.

\* cited by examiner

FIG. 1
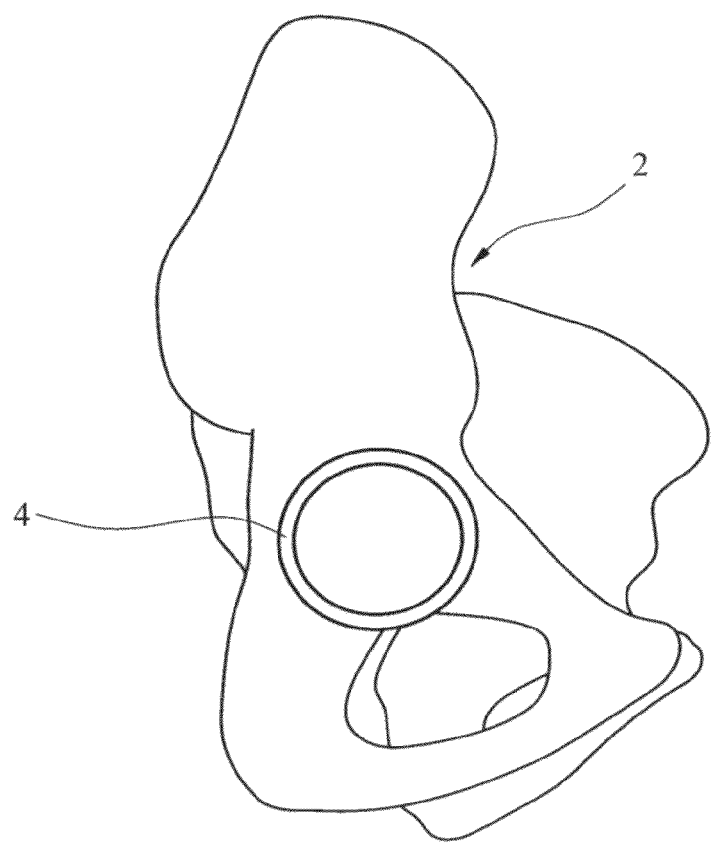
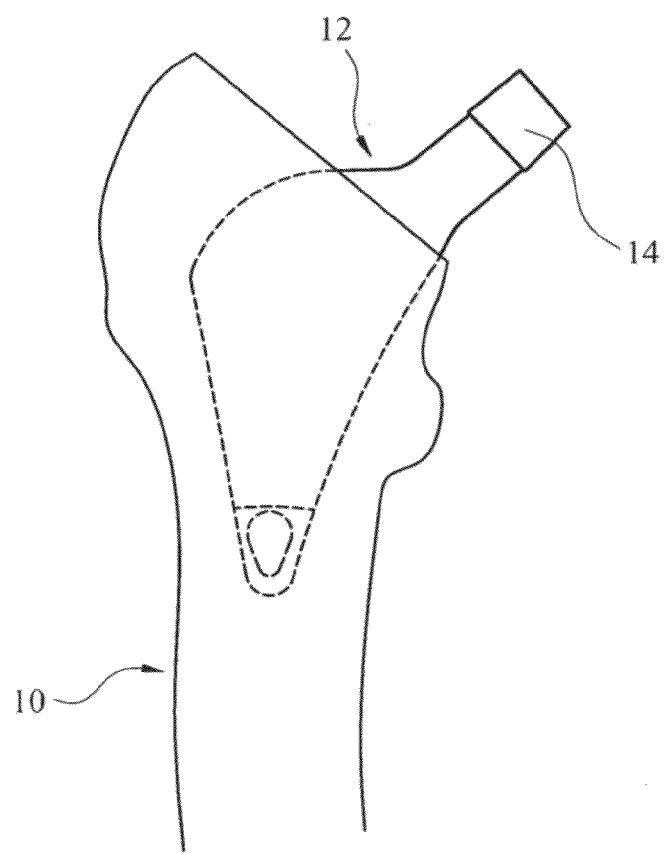
FIG. 2

HEAD COMPONENT OF AN ORTHOPAEDIC JOINT PROSTHESIS

CROSS REFERENCE TO RELATED APPLICATION

The present application is a continuation of International Patent Application PCT/GB2008/001052 filed Mar. 27, 2008.

BACKGROUND OF THE INVENTION

This invention relates to a head component of an orthopaedic joint prosthesis.

Shoulder and hip joint prostheses include a convex head component and a concave socket component. The head component can be provided on a stem component which can be implanted in the femur or the humerus. In this construction, the socket component is fixed against movement by implantation in the acetabulum or the glenoid respectively. Especially in shoulder prostheses, it is also known for the socket component to be provided on a stem component (for implantation in the humerus) for articulation with a fixed convex head component (which is implanted in the glenoid).

A modular component which comprises a head component and a stem component can be assembled using a mating tapered spigot and socket assembly. For example, the stem component can have a tapered spigot, and a correspondingly tapered socket can be formed in the head component. Such assembly arrangements are well known.

The formation (spigot or socket as the case might be) which is provided in the head component might be located eccentrically. This can enable the head component to be offset relative to the axis of the stem component. The orientation of the offset can be adjusted by rotating the head component relative to the stem component.

It can be difficult to determine the angular orientation of the head component relative to another with which it is to be assembled for use.

BRIEF SUMMARY OF THE INVENTION

The present invention provides a head component of an orthopaedic joint prosthesis which has a chamfer surface between the convex bearing surface and a surface at which the component is connected to another component of the prosthesis.

Accordingly, in one aspect, the invention provides a kit for use in a procedure for implantation of an orthopaedic joint prosthesis, which comprises:
  a. a head component of an orthopaedic joint prosthesis, which comprises a body part having a convex bearing surface, and a reverse face at which the head component can be connected to a mating component of the joint prosthesis, in which the head component has a chamfer surface extending around at least part of its periphery where the bearing and reverse faces come together, and a plurality of markings on the chamfer surface,
  b. a trial head component which comprises a body part having a convex trial bearing surface and a reverse face, in which the trial head component has a plurality of markings on the trial bearing surface at or towards the interface between it and the reverse face,
in which the transverse dimensions of the head component are approximately the same as the transverse dimensions of the trial head component, and in which the location of the markings on the chamfer surface around the periphery of the head component corresponds to the location of the markings on the trial bearing surface of the trial head component around its periphery.

The kit of the invention has the advantage that markings can be provided on the chamfer surface to provide an indication of the angular orientation of the head component relative to the other component with which the head component is mated in the assembled joint prosthesis. By appropriate orientation of the chamfer surface, its provision allows the markings to be provided on a surface which is visible to the surgeon. Furthermore, the bearing surface can remain free of markings which has benefits in terms of minimising wear of the bearing surface with which the bearing surface on the head component articulates. Markings can be provided using a marking material which has a contrasting appearance relative to the appearance of the chamfer surface. The markings should be capable of withstanding exposure to materials and conditions to which they are exposed during use of the component without being eroded or otherwise made less visible. It can be preferred to form the markings by an etching technique; a preferred technique for forming the markings is laser etching.

The finish of the chamfer surface will generally be different from the finish of the bearing surface. The bearing surface should be finished so that it is smooth and highly polished, to the standards which are well established for metal bearing surfaces of orthopaedic joint prostheses, for example with a surface roughness of not more than 0.05 μm $R_a$. The chamfer surface can be less finely finished than the bearing surface, in particular so as to optimise the visibility of markings on the bearing surface. It can be preferred for example that the chamfer surface has a generally matt appearance relative to the highly polished finish of the bearing surface. For example, the surface roughness of the chamfer surface might be at least about 0.3 μm $R_a$, or at least about 0.5 μm $R_a$, or at least about 0.7 μm $R_a$, or at least about 1.0 μm $R_a$.

The finish on the trial bearing surface of trial component will generally be less smooth or less polished or both than the bearing surface of the head component of the joint prosthesis. For example, the surface roughness of the trial bearing surface might be greater than 0.05 μm $R_a$, for example, at least about 0.1 μm $R_a$, or at least about 0.15 μm $R_a$, or at least about 0.2 μm $R_a$.

The trial component can have markings which extend on to the trial bearing surface. The markings can be provided in the form of surface markings. The markings can be indented into the trial bearing surface, for example in the form of grooves. The grooves can be used to locate an instrument by which reference marks can be made on a bone or other surface, for subsequent alignment of the head component of the joint prosthesis, using the markings on the chamfer surface thereof.

The reverse face of the trial component can have a feature on it by which the head component can be connected to the mating component of the joint prosthesis. Preferably, the feature is located eccentrically. The connection between the trial component and the mating component of the joint prosthesis will be required to be temporary. Otherwise, the nature of the connection will be similar to that between the head component and the mating component. Preferably, the connection feature on the trial component comprises a socket in which a spigot on the mating component of the joint prosthesis can be received.

It will generally be preferred that each of the trial component and the head component has at least two markings spaced apart around its periphery. For example, each of the trial component and the head component can have three spaced apart markings. The relative locations of the markings on the head component around its periphery should correspond to the relative locations of the markings on the trial head component around its periphery. For example, the angles subtended at the axes of the components between adjacent markings should be the same. When there is more than one marking, it will generally be preferred that the markings can be distinguished from one another.

The transverse dimensions of the head component and the trial head component should be approximately the same. For example, the head component and the trial head component should have approximately the same diameter (when they have a circular shape) at the interface between the bearing surface and the reverse face. It will generally be preferred that corresponding transverse dimensions of the head component and the trial head component differ by less than about 10%, especially less than about 5%.

The shapes of the head and trial head components should be approximately the same, at least in general outline. It is important that the head component is configured to provide the desired bearing characteristics after implantation. The trial head component can omit features of the head component which are not required in view of the fact that it is only used during the implantation procedure and is not intended to be implanted permanently in a patient. The trial head component can have additional features which are appropriate for its use during the implantation procedure.

Preferably, the chamfer surface is planar when the component is viewed in cross-section. It is envisaged that the planar chamfer surface might be rounded slightly where it joins one or each of the bearing and connection surfaces.

Preferably, the convex bearing surface of the body part defines a polar axis thereof, and the angle between the chamfer surface and the polar axis is at least about 10°, more preferably at least about 15°, especially at least about 20°, for example at least about 25°, especially about 30°.

Preferably, the angle between the chamfer surface and the polar axis is not more than about 70°, more preferably not more than about 60°.

Preferably, the convex bearing surface of the body part forms part of a sphere. For many applications, it will be preferred that the bearing surface subtends an angle at the centre of the sphere of at least about 200°, more preferably at least about 240°, for example at least about 270°.

Preferably, the radius of the sphere is at least about 8 mm, more preferably at least about 10 mm, especially at least about 15 mm. Preferably, the radius of the sphere is not more than about 35 mm, more preferably not more than about 25 mm.

Preferably, the convex bearing surface of the body part defines a polar axis thereof, and the width of the chamfer surface measured from the convex bearing surface to the connection surface in a plane which contains the polar axis is at least about 3 mm. The line at which the chamfer surface joins the connection surface will often be planar. Preferably the width of the chamfer surface measured from the convex bearing surface to the connection surface in a plane which is perpendicular to the plane which is defined by the line at which the chamfer surface joins the connection surface is at least about 3 mm. Preferably the width of the chamfer surface is at least about 5 mm. The width of the chamfer surface will generally be not more than about 10 mm, preferably not more than about 8 mm.

It will generally be preferred that the chamfer surface has a marking formed on it to identify a position on the head component around the periphery thereof. The marking might be provided by laser etching. Other techniques which might be used include engraving.

The connection surface will usually have a feature on it by which the head component can be connected to the mating component of the joint prosthesis, and in which the feature is located eccentrically. The feature might be a socket in which a spigot on the mating component can be received. The feature might be a spigot in which a socket on the mating component can be received. The spigot should be a tight fit in the socket. Preferably, the spigot and the socket are tapered so that there is an interference fit between the mating surfaces when the parts are assembled. As is known, for many combinations of materials, appropriate locking an be achieved when the angle between the surface and the axis of the part in question is in the region of, for example, from about 2.5° to about 5°.

In another aspect, the invention provides a kit which includes an additional component which can be mated with the head component. The additional component might have a stein part which can be fitted so that it extends into an intramedullary cavity.

It will generally be preferred for the head component to be formed from one or more of a metal and a ceramic material. Suitable metals for use in the manufacture of these parts include certain stainless steels, titanium and its alloys, and alloys which include cobalt and molybdenum. Suitable ceramic materials include certain oxides, nitrides and carbides of elements such as aluminium, zirconium, titanium and so on.

BRIEF DESCRIPTION OF THE DRAWINGS

Embodiments of the invention will now be described by way of example with reference to the accompanying drawings, in which:

FIG. 1 is a view of a prepared acetabulum, in which an acetabular cup component has been implanted.

FIG. 2 is a view along the anterior posterior axis of the head of a femur, in which a stem part of a femoral component of a hip joint prosthesis has been implanted.

DETAILED DESCRIPTION OF THE INVENTION

Figure 3:
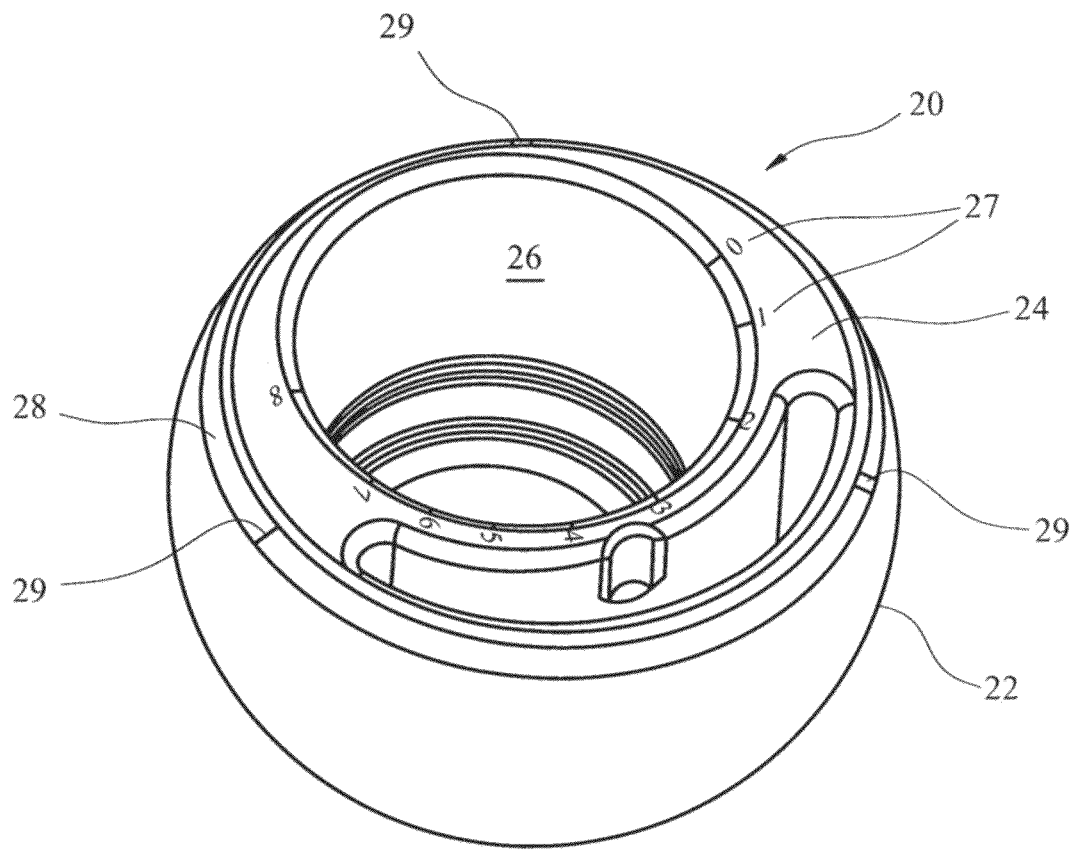
FIG. 3 is a view from below of a head part of a femoral component.

Referring to the drawings, FIG. 1 shows a pelvis 2 which is been reamed to receive the acetabular cup component 4 of a hip joint prosthesis. The acetabular cup component has been implanted using conventional techniques.

FIG. 2 shows the head portion of a femur 10 which has been resected at the base of the femoral neck. The intramedullary cavity has been prepared using conventional techniques (by reaming or broaching or a combination of the two) to receive the stem part 12 of the femoral component of a hip joint prosthesis. The stem part can be fastened in the femur by means of a bone cement material, as is known. The stem part can be fastened in the femur without the use of a bone cement material, as is known.

The stem part has a tapered spigot 14 at its exposed end on which the head part of the femoral component can be fitted. The dimensions of the spigot on the stem part are in line with existing stem parts of femoral components of hip joint prostheses.

FIG. 3 shows the head part 20 of a femoral component of a hip joint prosthesis according to the present invention. The head part has a spherical bearing surface 22 and an opposite reverse face 24. The spherical bearing surface extends through an angle of arc of about 200°. The radius of the bearing surface is 18 mm. The distance from the reverse face of the head part to the point where the polar axis intersects the bearing surface is from 28.25 to 41.8 mm.

A tapered bore 26 is formed in the reverse face 24. The bore has a circular cross-section. At the reverse face, the diameter of the bore is from 24.2 to 28.6 mm. The depth of the bore, measured from the reverse face of the head part to the blind end of the bore, is from 9.0 to 11.5 mm. The angle between the wall of the bore and its axis (which is half of the angle defined by the diametrically opposite walls of the bore) is 5°.

The bore 26 is offset relative to the polar axis (which is the axis extending through the centre of the sphere defined by the bearing surface, perpendicular to the reverse face). The distance between the axis of the bore and the polar axis is from 2 to 4 mm.

The head part has a series of markings 27 on its reverse face. These relate to the distance through which the head part is offset relative to the axis of the stem part when the femoral component is assembled, as discussed below.

The head component has a chamfer surface 28 extending around its periphery where the chamfer and reverse faces come together. The chamfer surface is planar when the component is viewed in cross-section. The angle between the chamfer surface and the polar axis is about 50°. The chamfer surface has three markings 29 at spaced apart points. The markings are distinguishable from one another.

Figure 4:
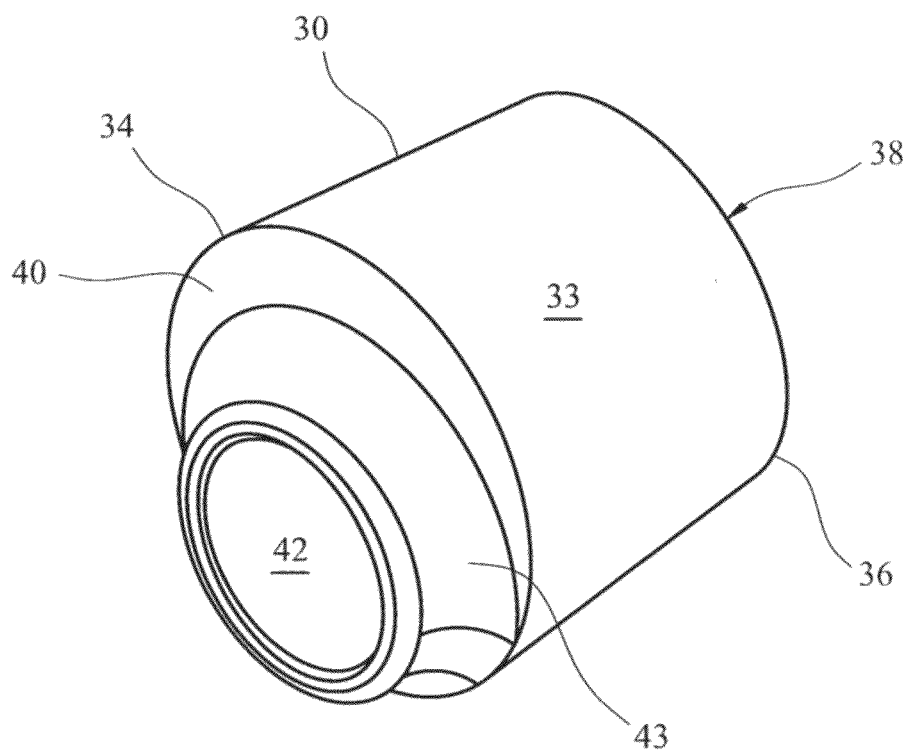
FIG. 4 is an isometric view from below of a connector in place which can be used to connect the head part shown in FIG. 3 to the stem part shown in FIG. 2.

FIG. 4 shows a connector 30 which can be used to connect the head part to the stem part 12 of the femoral component. The connector is circular when viewed from above and is tapered inwardly along the axis defined by its external surface 32. The diameter of the connector at its widest 34 point is from 24.2 to 28.3 mm. The diameter of the connector at its narrowest point 36 is from 22.45 to 20.7 mm. The depth of the connector measured from its top face 38 to its opposite bottom face 40 (not including the skirt which depends from the bottom face) is from 19.75 to 22.25 mm. The angle between the wall of the connector and its axis (which is half of the angle defined by the diametrically opposite walls of the connector) is 5°. The connector is therefore a snug fit in the bore 26 in the head part, with the top face 38 located within the bore 26 in the head part, and the bottom face 40 located adjacent to the reverse face 24 of the head part. When the connector is fully received in the bore 26 in the head part, the length of the contacting surfaces of the connector and the bore, measured along the axis of the bore, is from 19.75 to 22.25 mm. The widest point at which the connector is in contact with the bore is at the widest part of the connector part (that is at the bottom face 40). Accordingly, the ratio of the length of the contacting surfaces of the bore in the head part and the connector part when assembled, measured along the axis of the bore in the head part, to the diameter of the bore in the head part at the widest point at which it contacts the external surface of the connector part, is 1.23 (24.2:19.75) or 1.27 (28.3:22.25) in the two embodiments which are discussed.

The connector 30 has a bore 42 within it extending from the bottom face 40. The bore is tapered inwardly in a direction away from the bottom face of the connector. The bore is open at its opposite narrow end. The bore can be blind at its narrow end. A skirt 43 surrounds the bore at its open end on the bottom face 40.

The bore 42 in the connector is sized so that the spigot 14 on the stem is a snug fit within it.

Figure 5:
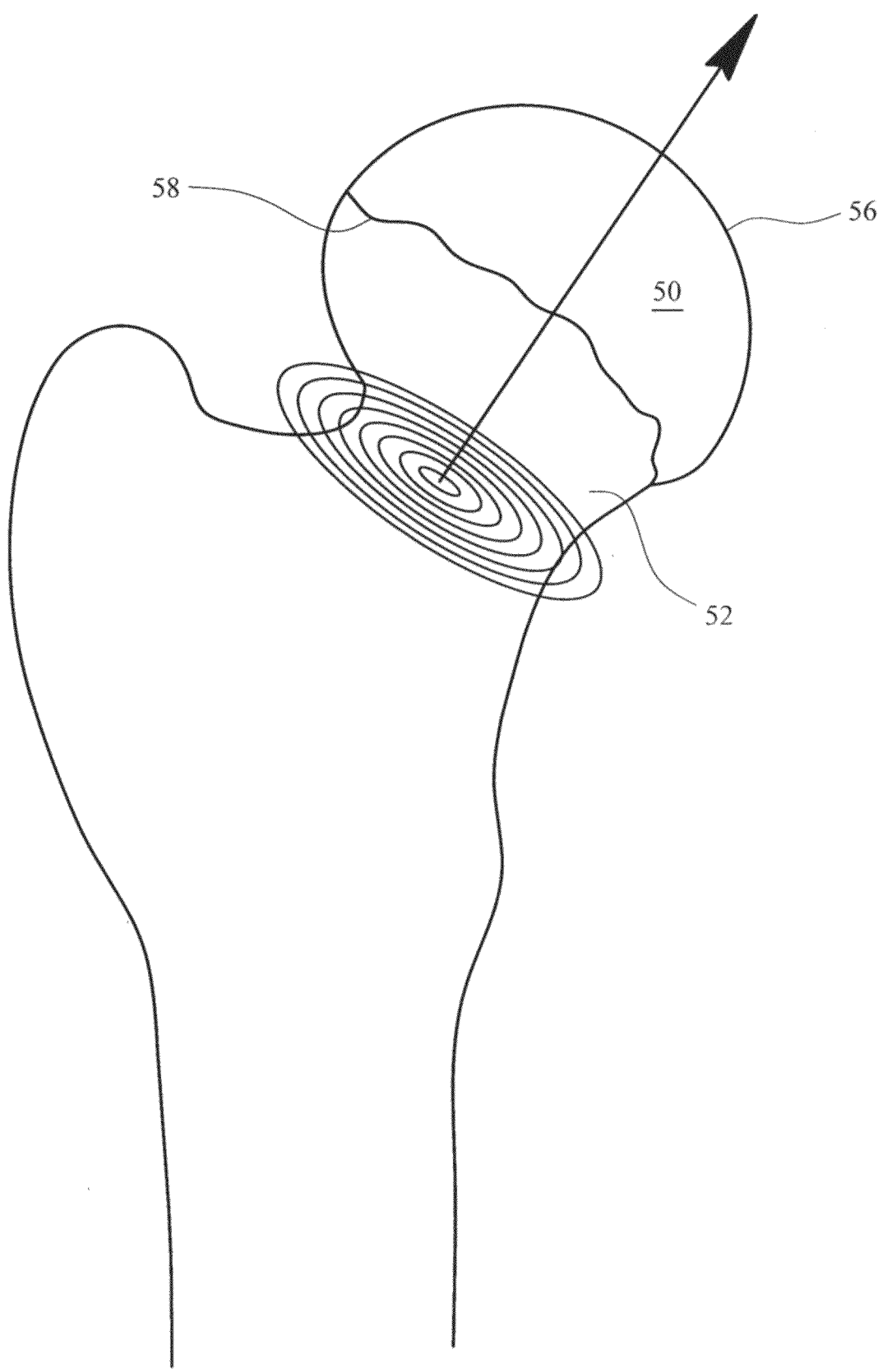
FIG. 5 is a view of the head of a femur to illustrate the offset of the bearing surface of the femoral head relative to the femoral neck.

FIG. 5 shows the head portion of a femur prior to any resection step in a procedure for replacement of a hip joint. The femur has a head part 50 and a neck 52 which extends between the head part and the femoral shaft 54. The outer bearing surface 56 of the head part is smooth, for articulation with a corresponding bearing surface within the acetabulum, and extends over the head part towards the femoral shaft to a boundary line 58. The bearing surface of the head part is defined by part of a sphere. The axis of the head part passes through the centre of the sphere, in a direction which is perpendicular to the plane which is defined by the boundary line 58.

The femoral neck 52 defines an axis which extends along its central core, between the femoral shaft and the head part.

The head part 50 of the femur can be offset relative to the femoral neck. A translational offset arises when there is a gap between the axis of the head part and the axis of the femoral neck. The size of the gap between the axes can be different from one patient to another, for example in the range 0 to 10 mm. The direction in which the axes are offset can vary, around the axis of the femoral neck.

Figure 6:
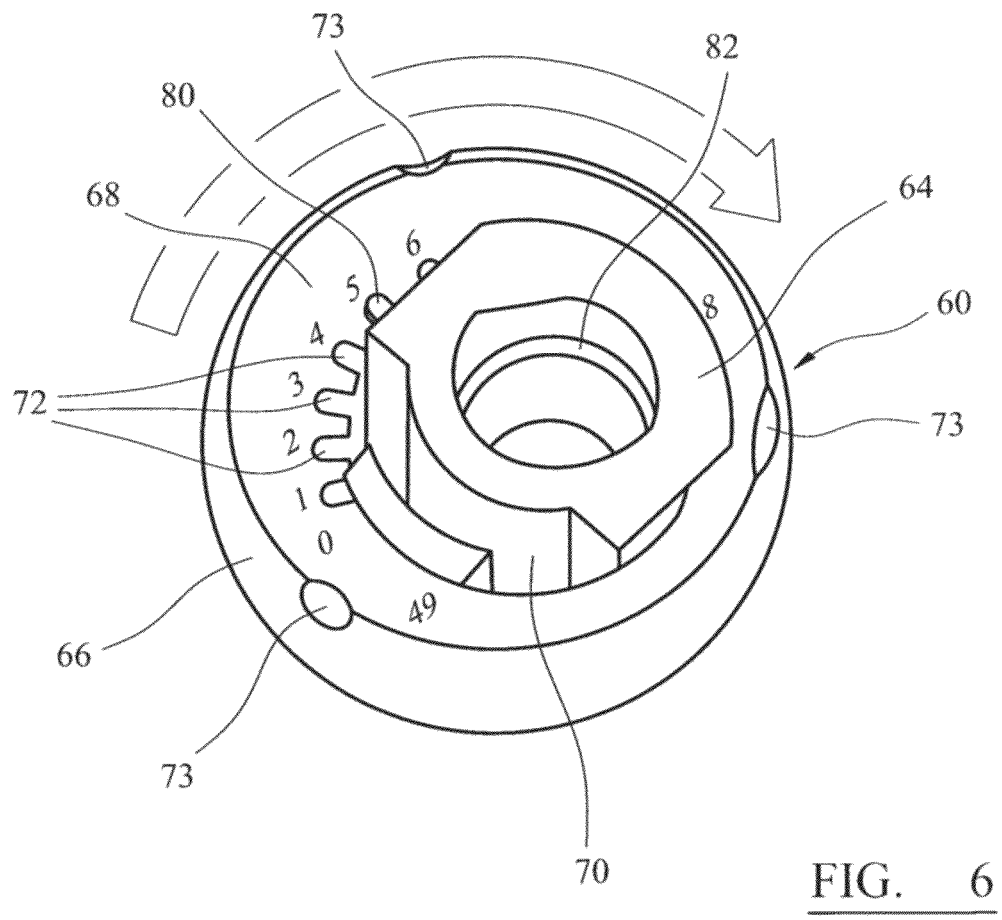
FIG. 6 is a view from below of a trial instrument which can be used to select the appropriate offset in an assembled femoral component.
Figure 7:
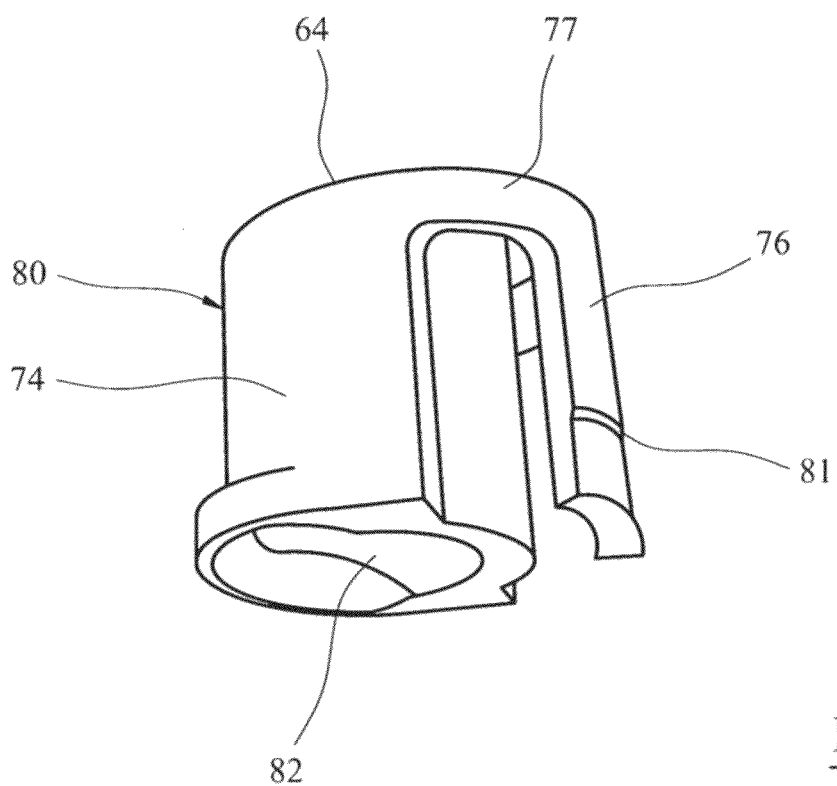
FIG. 7 is a side view of the trigger part of the trial instrument which is shown in FIG. 6.
Figure 8:
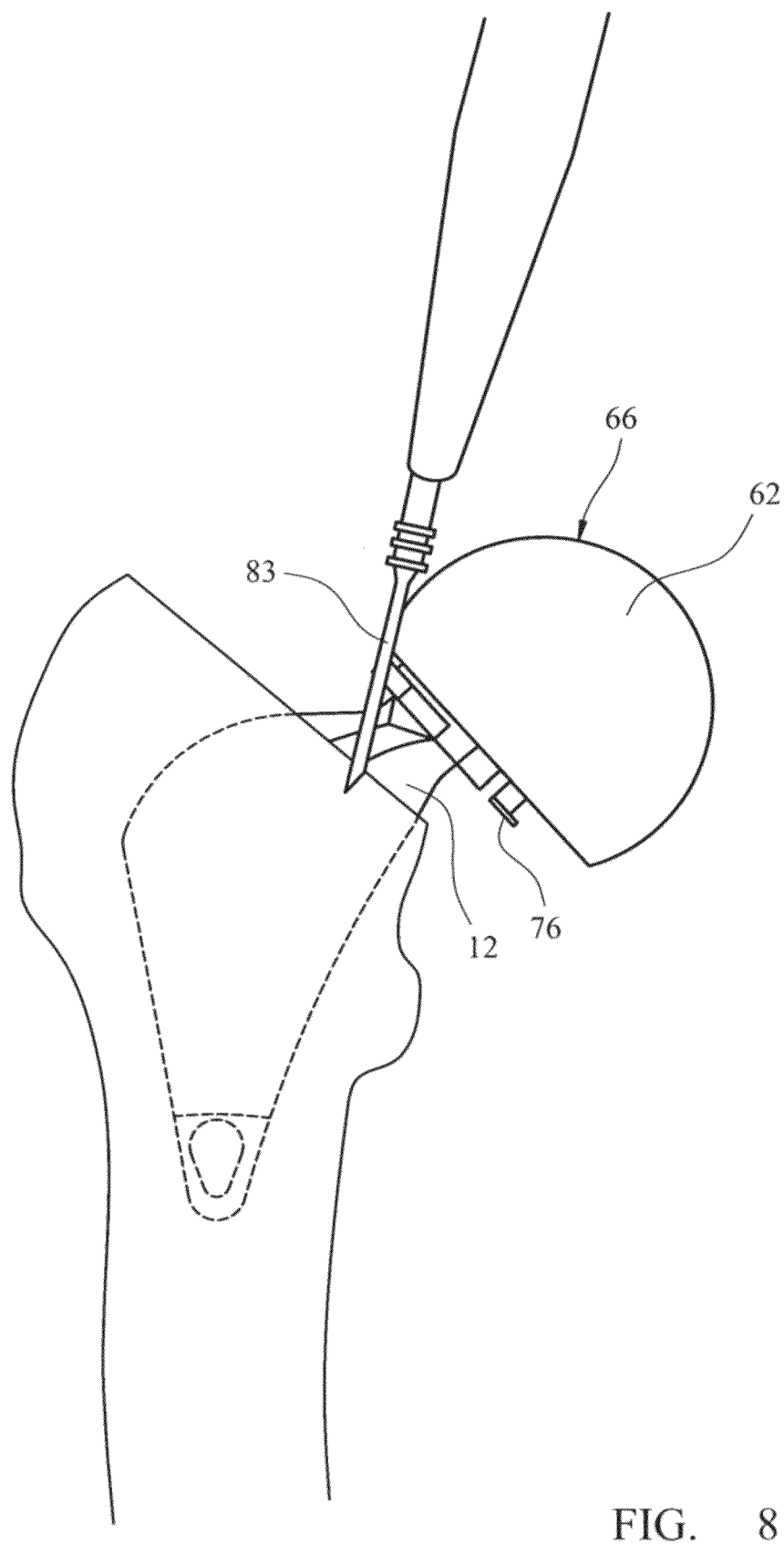
FIG. 8 is a side view of the head of the femur, with the trial instrument shown in FIG. 6 mounted on the stem part.

FIG. 6 shows an instrument 60 which can be used to trial the head part (with its connector) on an implanted stem part. The instrument comprises a trial head part 62 and a trial connector 64. The trial connector is shown in FIG. 7. The trial head part has a spherical outer surface 66 which corresponds to the bearing surface of the head part of the ultimate implant, and an opposite reverse face 68. The head part has a recess 70 within it extending inwardly from the reverse face towards the bearing surface. The recess is generally round when The recess has a plurality of grooves 72 in its side wall extending parallel to the axis of the recess. The trial head part can be formed from a metal such as a stainless steel or from a polymeric material.

The spherical outer surface 66 of the trial head part has three notches 73 at spaced apart points. The notches are distinguishable from one another, for example by means of distinguishing markings located adjacent to the notches.

The trial connector 64 is formed from a polymeric material. It comprises a body part 74 and a trigger 76 which is connected to the body part at one end 77. The material of the trigger 76, and of the body part when the trial connector is formed as a single piece) is sufficiently resilient that the trigger can be deformed inwardly towards the body part.

The body part has a rib 80 which is dimensioned so that it can fit into one of the grooves 72 in the side wall of the recess.

The trial head part and the trial connector have locking features so that the connector is retained within the recess 70 in the head part when the trigger is released, and can be removed from within the recess when the trigger is deformed towards the body part. The locking features can comprise an annular groove which extends around the recess, and a rib 81 on one or each of the body part and the trigger of the trial connector. When the rib is received in the groove, the trial connector is locked against removal from the bore in the trial head part. When the trigger 76 is squeezed towards the body part 74, the trial connector is able to move transversely within the recess in the body part so that the rib can be withdrawn from the groove, allowing the trial connector to be withdrawn from within the recess.

The body part 74 of the trial connector has a bore 82 formed in it. The bore is tapered inwardly in a direction away from the bottom face of the connector. The bore is open at its opposite narrow end. The bore is blind at its narrow end. The bore 82 in the trial connector is sized so that the spigot 14 on the stem is a snug fit within it.

Figure 9:
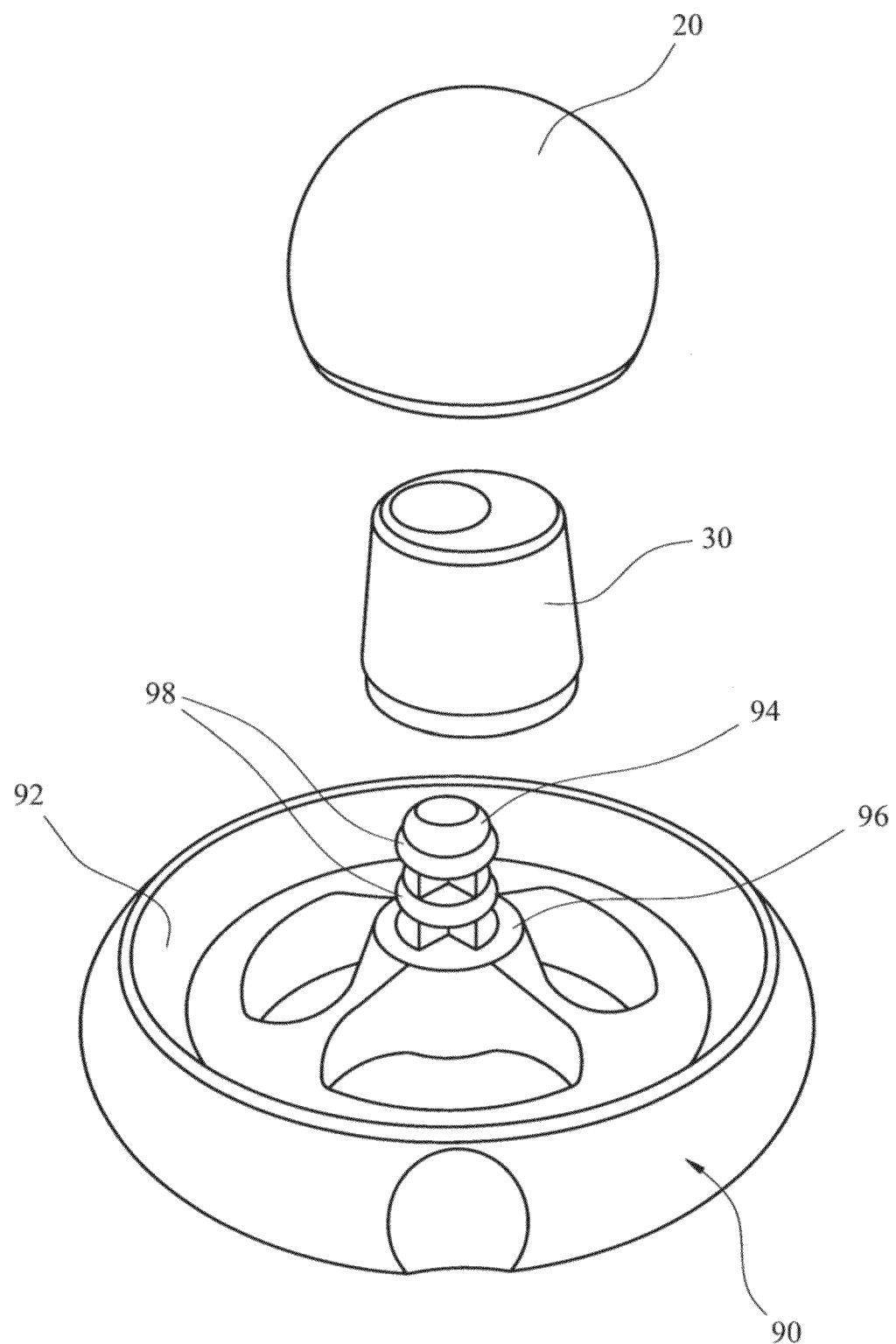
FIG. 9 is a side view of a tool which can be used to assemble the head part and the connector, shown in FIGS. 3 and 4 respectively.

FIG. 9 shows an assembly tool 90 which can be used in the assembly of the head part 20 of the femoral component and the connector 30. The tool comprises a base 92 having an upstanding spigot 94. The spigot has a collar 96 around it, which presents an upwardly facing surface. A pair of compressible O-rings 98 are provided on the spigot, located in annular grooves therein. The sizes of the spigot and the O-rings are such that the O-rings are compressed on contact with the internal wall of the bore 42 in the connector 30 when the connector is seated on the tool with the bottom face of the skirt 43 in contact with the collar 96 on the tool. This can help to retain the connector on the spigot, by virtue of the friction forces between the O-rings and the internal surface of the bore in the connector.

The assembly tool 90 is made from stainless steel. It can have a ring of a rubber material located in a groove in its lower face such that it protrudes from the groove to engage the surface on which the tool is placed when in use.

Figure 10:
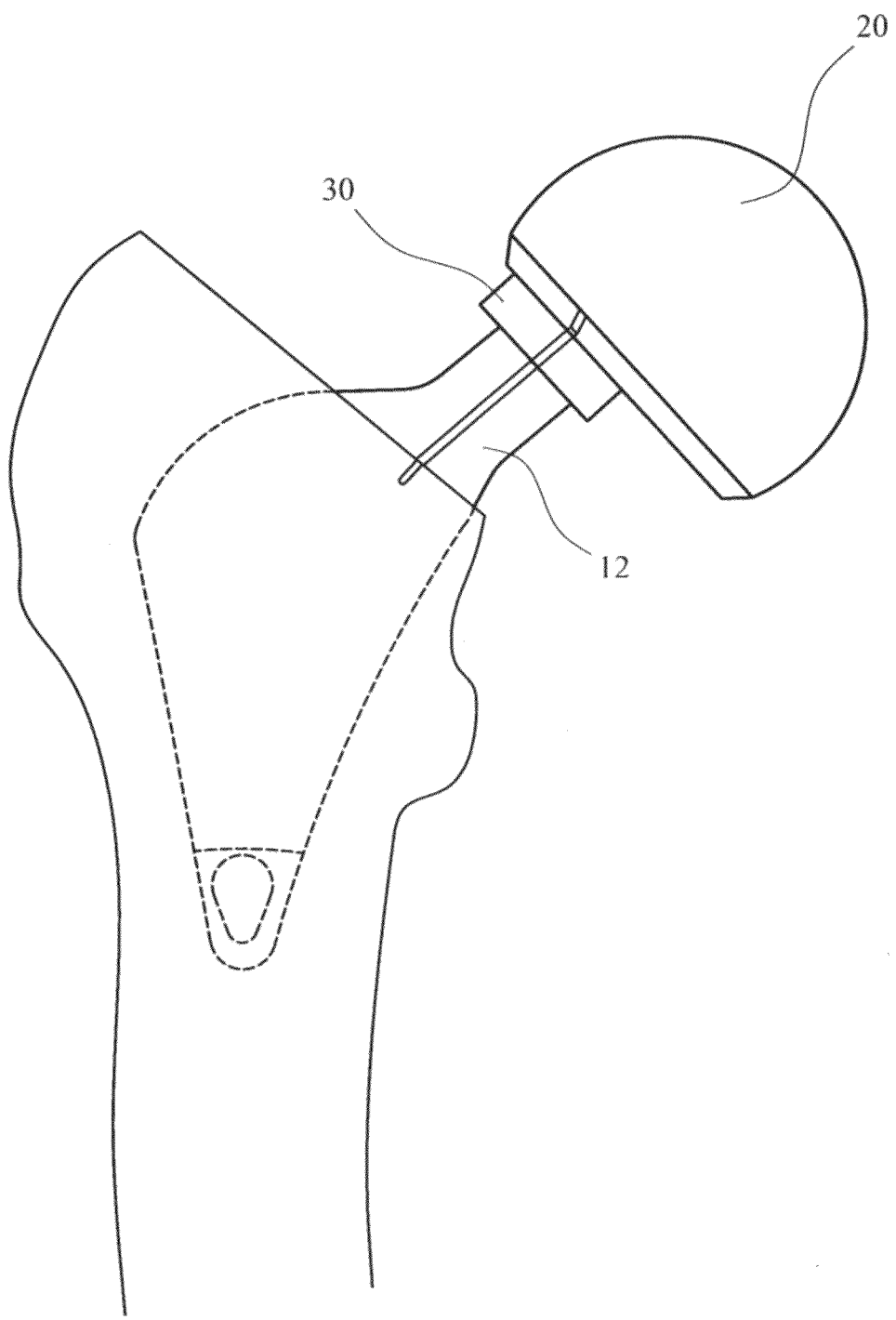
FIG. 10 is a view from one side of an assembled femoral component of a hip joint prosthesis according to the present invention.

FIG. 10 shows the femoral component of a hip joint prosthesis according to the present invention which has been assembled. The assembled femoral component comprises the head part 20, with the connector 30 located in the bore 26 therein. The spigot 14 on the stem part 12 of the femoral component is located in the bore 42 in the connector.

A procedure in which the invention can be implemented to provide a femoral component of a hip joint prosthesis can include the following steps.

Initial steps involve preparing the femur to receive the stem part. These steps are conventional, and include resection of the neck and head of the femur, and working on the intramedullary cavity in the femoral shaft so that it is appropriately dimensioned to receive the stem part.

Preparatory work on the patient might provide information as to the desired offset of the femoral head. The trial components described above with reference to FIGS. 4 to 6 can allow offsets to be assessed. Variations in the size of the gap between the axis of the head part and the axis of the femoral neck can be replicated by changing the angular relationship between the trial head part 62 and the trial connector 64, using the trigger to release the trial connector for movement in the recess in the trial head part. Variations in the direction in which the axes are offset can vary, around the axis of the femoral neck, can be replicated by rotating the trial components around the spigot 14 on the stem part 12.

Markings on the reverse face 68 of the trial head part 62 provide an indication of the size of the offset, which is then to be incorporated in the assembled head component.

A record of the angular orientation of the trial head part about the spigot 14 is made with reference to a selected one of the notches 73 on the spherical outer surface 66 of the trial head part, using a diathermy 83 to make a mark on bone tissue 84 immediately below the selected notch.

The size of the offset that is determined using the trial head part and the trial connector are reproduced in the head component with reference to the markings 28 on the reverse face 24 of the head part 20 (which are the counterparts to the grooves 72 in the side wall of the recess 70 in the reverse face 68 of the trial head part 62), and to a marking on the connector 30 (which is the counterpart to the rib 80 on the trial connector 64). The head part 20 and the connector 40 of the implant are assembled accordingly, and placed on the spigot 94 of the assembly tool 90. An impaction force is applied to the head part through an appropriate protector (such as a block of polyethylene which is configured to be a conforming fit on the bearing surface 22 of the head part 20). Application of the impaction force causes the connector to be forced downwardly on to the spigot 94 until the skirt 43 on the bottom face of the connector contacts the collar 96 on the tool, compressing the O-rings 98 on the spigot as necessary. When the skirt on the connector contacts the collar on the tool in this way, applied impaction force leads to securing of the connection between the head part 20 and the connector 40.

The assembled head component (comprising the head part 20 and the connector 40) is positioned on the spigot 14 on the stem part 12. The alignment of the head component on the stem part offset that is determined using the trial head part and the trial connector are reproduced in the head component with reference to a selected one of the markings 29 on the chamfer surface 28 which corresponds to the selected notch on the trial head part which was used previously to make a mark on the bone using the diathermy.

An impaction force is applied to the head component through an appropriate protector (such as a block of polyethylene which is configured to be a conforming fit on the bearing surface 22 of the head part 20) to cause the head component to become secured to the stem part. This is in line with existing assembly techniques for use with orthopaedic joint prostheses.

The invention claimed is:

1. A kit for use in a procedure for implantation of an orthopaedic joint prosthesis, comprising:
    a head component having a periphery and an axis, the head component comprising a convex bearing surface, a reverse face, and a chamfer surface extending around at least part of the periphery, and wherein the head component has a maximum width, the reverse face has a width that is less than the maximum width of the head component, the chamfer surface extends inwardly from the bearing surface toward the axis and connects the bearing surface and the reverse face, and the chamfer surface has a plurality of markings; and
    a trial head component comprising a body part having a convex trial bearing surface and a reverse face, wherein the trial head component has a plurality of markings on the trial bearing surface at or towards the interface between the bearing surface and the reverse face, wherein the transverse dimensions of the head component are approximately the same as the transverse dimensions of the trial head component, and wherein the location of the plurality of markings on the chamfer surface of the head component corresponds to the location of the plurality of markings on the trial bearing surface of the trial head component.

2. The kit of claim 1, wherein the plurality of markings comprises three markings spaced apart around the periphery.

3. The kit of claim 1, wherein the chamfer surface is planar when the head component is viewed in cross-section.

4. The kit of claim 1, wherein the convex bearing surface of the body part defines a polar axis, and wherein the angle between the chamfer surface and the polar axis is at least about 10°.

5. The kit of claim 4, wherein the convex bearing surface of the body part defines a polar axis thereof, and wherein the angle between the chamfer surface and the polar axis is not more than about 60°.

6. The kit of claim 1, wherein the convex bearing surface of the body part forms part of a sphere.

7. The kit of claim 1, wherein the bearing surface subtends an angle at the center of the sphere of at least about 200°.

8. The kit of claim 7, wherein the radius of the sphere is at least about 8 mm.

9. The kit of claim 7, wherein the radius of the sphere is not more than about 35 mm.

10. The kit of claim 1, wherein the convex bearing surface of the body part defines a polar axis, and wherein the width of the chamfer surface measured from the convex bearing surface to the reverse face in a plane that contains the polar axis is at least about 1 mm.

11. The kit of claim 1, wherein the convex bearing surface of the body part defines a polar axis, and wherein the width of the chamfer surface measured from the convex bearing surface to the reverse face in a plane that contains the polar axis is not more than about 8 mm.

12. The kit of in claim 1, wherein the reverse face has a connection feature located thereon by which the head component is connected to the mating component of the joint prosthesis, and wherein the feature is located eccentrically.

13. The kit of claim 12, wherein the connection feature comprises a socket dimension to accept a spigot on the mating component of the joint prosthesis.

14. A joint prosthesis, comprising the kit of claim 1, and an additional component that can be mated with the head component.

15. A joint prosthesis as claimed in claim 14, wherein the additional component has a stem part dimensioned to be positioned such that the stem part can extend into an intramedullary cavity.

16. The joint prosthesis of claim 15, wherein the head component has a socket formed therein extending inwardly from the reverse face, and wherein the additional component has a spigot formed thereon that is dimensioned to fit in the socket.

* * * * *